United States Patent
Stihler et al.

[11] Patent Number: 5,474,538
[45] Date of Patent: Dec. 12, 1995

[54] APPARATUS FOR THE WARMING OF FLUIDS IN MEDICAL APPLICATIONS

[75] Inventors: Axel Stihler, Gerlingen; Wolfgang Theilacker-Beck, Stuttgart, both of Germany

[73] Assignees: Stihler Electronic medizinische Geräte Produktions; Vertriebs GmbH, both of Stuttgart, Germany

[21] Appl. No.: 373,314
[22] PCT Filed: Jul. 13 1993
[86] PCT No.: PCT/DE93/00624
  § 371 Date: Jan. 17, 1995
  § 102(e) Date: Jan. 17, 1995
[87] PCT Pub. No.: WO94/02189
  PCT Pub. Date: Feb. 3, 1994

[30] Foreign Application Priority Data

Jul. 17, 1992 [DE] Germany ............... 42 23 521.9

[51] Int. Cl.⁶ .................................................. A61F 7/12
[52] U.S. Cl. ................... 604/113; 606/24; 607/96
[58] Field of Search ................... 604/113, 4, 28; 606/24, 27; 607/96, 104, 105

[56] References Cited

U.S. PATENT DOCUMENTS 3,551,641  12/1970  Truhan ........................... 604/113 X
5,269,749  12/1993  Koturov ......................... 604/113 X

FOREIGN PATENT DOCUMENTS 0181447  8/1985  European Pat. Off. .
0444011  2/1991  European Pat. Off. .
3606930  3/1986  Germany .
9209604  7/1992  Germany .

*Primary Examiner*—John D. Yasko
*Attorney, Agent, or Firm*—Thomas R. Vigil

[57] ABSTRACT

The apparatus for the heating of fluids exhibits a cylindrical heat exchanging body 10 which exhibits an outer groove 18 for the insertion of a conduit 20 through which the fluid is flowing. The groove 18 forms windings w with a heat transfer length 1 per winding w. With a fixed section length L to be warmed of the conduit 20, the heat transfer length 1 per winding w is at least increased by a factor of 1.4 or the heat exchanging cylinder 10 is directed largely horizontally and the diameter of the heat exchanging body 10 is larger or equal to 160 mm. (FIG. 1).

8 Claims, 3 Drawing Sheets

APPARATUS FOR THE WARMING OF FLUIDS IN MEDICAL APPLICATIONS

This application is a 371 of PCT/DE93/00624 filed Jul. 13, 1993.

BACKGROUND OF THE INVENTIONS

The invention concerns a medical warming apparatus for infusion, transfusion, and/or cleansing solutions with a regulatable and/or controllable heating device, acting on a conduit for the fluids, which warms a cylindrical heat exchanging body exhibiting a groove on the outer side for the insertion of the conduit through which the fluid is flowing and forming windings w with heat transfer length 1 per winding w.

An apparatus of this kind has become known in the art through publication EP 0 181 447 B1.

The apparatuses known in the art for the warming of infusions or transfusions having a cylindrically shaped heat exchanging body, exhibit a groove on the outer side, running in a screw-like fashion, for insertion of a conduit through which the fluid to be warmed flows. The heat exchanging bodies contained within apparatus housings are manufactured from a good heat conducting material in order to warm the fluid flowing in the conduit by contact heat transfer.

In the known apparatus in accordance with EP 0 181 447 B1, the heat exchanging body is directed vertically and the conduit arranged in the outer region of the heat exchanging body is covered with a heat protecting cuff. Using a groove shape which is adapted to the conduit and by covering the conduit running in the groove, it is possible to minimize the radiative heat losses and achieve, to a large extent, a uniform warming of the fluid flowing in the conduit. In another apparatus which is also part of prior art and which has become known through EP 0 444 011 A1 the heat exchanging body is configured as a horizontally directed straight circular cylinder and the conduit guiding the fluid is pressed into a groove running on the outer side of the circular cylinder. The groove is configured in such a fashion that, on the one hand, it is substantially deeper than the outer diameter of the conduit to be placed into the groove and the groove bottom is displaced relative to the groove opening. The groove exhibits side walls running from the groove bottom to the groove opening which present a narrowed region to the conduit to be placed into the groove along the entire depth of the groove.

In addition to these instruments an additional apparatus produced by the company Dideco (see EP 0 181 447 B1 column 1 lines 10 ff) is also known in the art which likewise exhibits a horizontally directed heat exchanging body configured as a straight circular cylinder.

In the apparatuses known in the art the heat transfer length to the conduit guiding the liquid is limited by the number of grooved loops on the heat exchanging body. If, as known in the art, the individual groove loops are arranged in closer proximity to each other, it is thereby only possible to lengthen the heat exchanging length by a limited amount and the ease use of the apparatus is reduced.

Conventional heat transfer lengths with cylindrical heat exchanging bodies are up to approximately 37 cm per loop (winding).

It is also necessary to take into account, excluding the apparatus in accordance with EP 0 181 447 B1, that, in addition to the limited heat transfer length, an uncontrolled convective heat loss also occurs in the outer region of the conventional heat exchanging cylinder which does not improve the efficiency of the effective warming of the fluid. Should the grooves be configured very deeply in the conventional heat exchanging cylinder, there is the additional danger that the struts between the grooves assume the function of cooling ribs over a large region to cancel out the advantages associated with the corresponding groove shape. Likewise with the conventional deeply configured groove cross sectional shapes it is not possible to easily check whether or not the conduits inserted into the groove seat tightly on the groove bottom. If this is not the case a strong reduction in heat transfer results.

Therefore the underlying problem of the invention is to further improve the conventional heat exchanging cylinder in such a fashion that the radiative losses to the environment are reduced.

SUMMARY OF THE INVENTION

This purpose is achieved in accordance with the invention in that, for a given length section L of the conduit to be warmed, the heat transfer length 1 per winding w assumes a value of at least 52 cm and the groove is fashioned in the vicinity of the opening from a heat insulating material or is coated with a heat insulating material.

In the event that the groove, in the vicinity of the opening, is fashioned from a heat insulating material or coated with a heat insulting material, it is possible for the shape of the groove to also exhibit a depth which is much larger than the outer diameter of the conduit. Undesired cooling effects of the rib-like groove struts are effectively compensated for.

In an embodiment of the invention the groove exhibits a groove opening which is at least 1,6 times larger than the outer diameter of the conduit.

This has the advantage that operational personnel can easily check, by way of example by probing with their finger tips, whether the conduit is completely seated in the groove. By means of the increased groove opening it is also possible for the conduit to be checked for seating in a deepened groove at the groove bottom. If the groove is thereby configured in such a fashion that it opens in a curved manner to form a first groove region with groove sides for inserting the conduit with an adjacent second holding groove region having groove sides for holding the conduit, whereby the groove sides of the first groove region are concave, convex or triangular-shaped and the groove sides of the second groove region tightly surround and, if appropriate, slightly press the conduit then, in addition to the increased ease of service, one still assures that the conduit does not incompletely seat on the bottom of the groove.

In an improvement of the apparatus in accordance with the invention one has the solution that the heat exchanging body is largely directed horizontally to an axis and the largest diameter dimension of the heat exchanging body exceeds 160 mm.

This has the advantage that multiple increases in heat transfer length are possible even with reduced numbers of groove loops. The length of the heat exchanging body in the axial direction can be kept short and the individual groove loops can be separated from each other in a manner which is easy to handle (large pitch) so that the conduit can be easily inserted into the groove. This type of heat exchanging body of larger perimeter also allows all control, regulating and operational components to be accommodated within the heat exchanging body itself, e.g. in the event that the heat exchanging body in accordance with the invention is configured horizontally and attached to a stand, it is thereby secured in a safer fashion than the conventional apparatuses. The torque exerted on a stand is small. The stand with its suspended heat exchanging body is therefore not susceptible to tilting. In the event that an increased efficiency is desired in conventional apparatuses, it is necessary for them to be lengthened and this produces, in the usual case, increased torques which can be compensated for only by opposing measures (for example counter weights).

In the apparatus in accordance with the invention such additional safety measures are not necessary since, due to its diametrical size, it is constructed in a very flat fashion and the weight of the apparatus acts closer to the stand post.

In the event that, with the apparatus in accordance with the invention, the heat exchanging body is, for example, configured as a straight circular cylinder with a diameter of about 225 mm, it is thereby possible to nearly double the heat transfer length per groove loop compared to the conventional apparatuses and to nearly half the depth of the apparatus. The heat exchanging body is thereby directed horizontally.

In a preferred embodiment the cross section of the heat exchanging body spans an area with respect to an axis which is circular or ellipsoidal.

This has the advantage that the heat exchanging body in accordance with the invention can be operated with simple hand motions. It is possible to insert the conduit in a very transparent fashion into the groove windings provided therefor and, with an elliptical cross sectional area, it is easy for the user to see over a substantial seating region whether or not and to what extent a, for example, conventional infusion set is properly seated and held in the groove.

If the heat exchanging body is configured as a hollow cylinder it can accept, in addition to the heating device, all operational elements and control elements without having these components project out of the hollow cylinder.

In a further configuration of the invention the groove runs in a screw-like fashion and the grooves exhibit a separation from each other, viewed in cross section along an axis of the heat exchanging body, which is larger than the groove width of a groove holding the conduit.

This has the advantage that, when winding the conduit onto the heat exchanging body, a groove loop is not unintentionally skipped to possibly induce a kink in the conduit. A conduit, when winding onto the heat exchanging body in accordance with the invention, is properly guided and, by means of the large separation between grooves, it is easier to wind the conduit. The enlarged diameter of the heat exchanging body thereby simplifies the winding motion of the operational personnel.

In a further embodiment the groove exhibits a groove bottom which lies within a groove opening of the corresponding individual groove. This has the advantage that the conduit can be pushed to the groove bottom by means of the main force component acting directly on the conduit. This groove form also allows, in the event of narrowings or of undercuttings of the groove with respect to the conduit, for its secure and proper seating on the bottom of the groove without requiring a larger expenditure of force or particular skill.

In a further embodiment, the apparatus for warming the liquid is defined by a first and a second end surface on the heat exchanging body. The operational components can be accommodated in the first end surface as well as a display and further components necessary for the operation of the device and, in the second end surface, the attachment grip can be accommodated by means of which the heat exchanging body can be attached to a stand. It is also possible with the heat exchanging body in accordance with the invention to create an apparatus which does not require any auxiliary housing components for the acceptance of operational components. A compact instrument for the heating of infusion and/or transfusion solutions is realized.

From ergonometric points of view, an axis of the heat exchanging body is directed largely horizontally with respect to a holding device, for example, a stand. Towards this end, it is advantageous if the heat exchanging body exhibits means for rotation and/or pivoting, whereby the heat exchanging body is, in particular, held to the holding device in a rotatable and/or pivotable fashion.

This has the advantage that, using simple means, namely through a rotation of a heat exchanging body or through a pivoting of the heat exchanging body, it is possible to check whether or not the conduit is properly seated in the groove provided therefor over the entire circumference of the heat exchanging body. Unintentional complications which can, as is known in the art, occur during a rapid and hasty insertion of the conduit into the groove can be obviated with the heat exchanging body in accordance with the invention, since it is possible to view the entire conduit run of the conduit through a simple rotating and/or pivoting of the heat exchanging body.

In a further embodiment of the invention, the groove is configured as a left-handed thread in going from a second end surface to a first end surface of the heat exchanging body. This has the advantage that right-handed individuals can rapidly, simply, and safely insert the conduit into the groove beginning at the left backward part and using circular rightward rotations of the hand.

In a further configuration of the invention, means for winding the conduit are provided for on or in the heat exchanging body, for example, a crank or an electrical drive. In the event that the heat exchanging body is provided with a crank or an electrical drive, it is necessary for the conduit to be pressed into the first groove loop, as viewed in plan view, at the back of the apparatus in the upper right portion and the conduit is then automatically pulled into the groove by means of a leftward rotation of the entire heat exchanging body. This further simplifies the insertion of the conduit.

In the event that means for warming a drip chamber provided for on a conduit are formed on or in the heat exchanging body, it is thereby guaranteed to a still larger extent that the fluid to be warmed reaches its designated warming temperature in as rapid a fashion as possible even at increased flow rates and an undesirable cooling, due for example to a requirement for a long conduit, can be effectively compensated.

In an advantageous embodiment the drip chamber can be snapped into a recess in the first or second end surfaces of the heat exchanging body in a detachable fashion. This has the advantage that it is not necessary to provide individual heating device for the drip chamber and the conduit run on the device for warming the fluid is not interfered with.

Clearly the conduit itself can also be insulated or heated in order to prevent undesirable cooling effects before and after the device for warming the fluid.

Further advantages can be derived from the description and the accompanying drawing. The above mentioned features and those which are to be further described below can likewise be utilized, in each case, in accordance with the invention individually or collectively in arbitrary combination. The embodiments mentioned are not to be considered as exhaustive enumeration, rather have exemplary character only.

The invention is represented in the drawing and will be more closely described in the embodiments.

Figure 1:
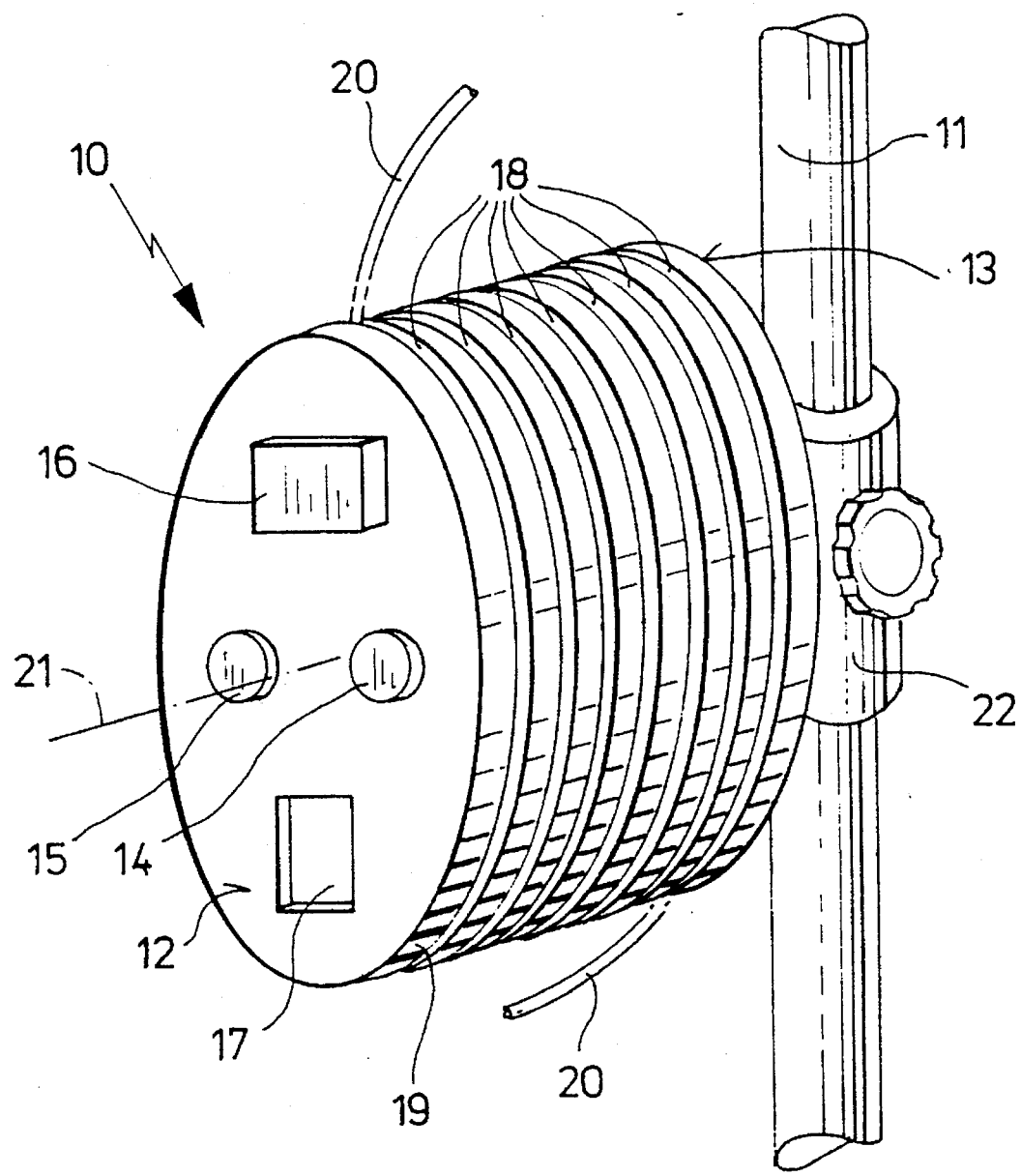
FIG. 1 shows an apparatus for the warming of fluids in a perspective view with a heat exchanging body having an elliptical-like cross section relative to an axis.

The individual figures of the drawing show the inventive subject in a strongly schematized fashion and are not to be taken to scale. The physical features of the individual figures are partially shown in a very enlarged fashion so that their construction can be more clearly shown.

DESCRIPTION OF THE PREFERRED EMBODIMENT

FIG. 1 shows a heat exchanging body 10 attached to a stand 11, by way of example an infusion stand. The heat exchanging body 10 is defined by a first end surface 12 and a second end surface 13. As shown in tile figure, the first end surface 12 is configured as a front plate by means of which the apparatus in accordance with the invention can be operated. An on-off switch 14 and a selection switch 15, which is not further described, for example for the adjustment or determination of the temperature desired in each case, are arranged on the front plate. 16 schematically indicates a display which optically shows tile desired values in each case. An opening 17 is provided on the front plate in which a drip and/or degasing chamber, which are not shown, can be snapped-in in a detachable fashion for optional heating. Grooves 18 are formed on a periphery of the elliptical-like heat exchanging body 10 which are separated from each other by means of struts 19 The grooves 18 run in a screw-like fashion over the outer surface of the heat exchanging body 10. The groove loops run, viewed towards the first end surface 12, in the manner of a left-handed thread travelling from the second end surface 13. A conduit 20 is indicated which guides the fluid to be warmed, in particular infusion and/or transfusion solutions. The conduit 20 is shown not inserted into the groove 18 so that the heat exchanging body 10 can he better shown. The groove 18 forms windings w on the outer surface of the heat exchanging body 10 with a heat exchanging length 1 per winding w. The heat exchanging length 1 is defined as follows $$l = \pi \cdot d \cdot w$$

whereby d corresponds to the diameter of a straight circular cylinder minus twice the groove depth. With arbitrary cylindrical heat exchanging bodies, d is a characteristic dimension corresponding to d of a straight circular cylinder.

In the event that a conduit 20 is inserted into the groove 18, a conduit section L of the conduit 20 is inserted into the groove 18, as viewed from above, at the rear left lower portion using a rightward circular shaped motion. The conduit 20 is only shown in sections. The conduit 20 leads downwardly to the patient and upwardly to the liquid container in which the liquid to be warmed to a particular temperature in the flow direction towards the patient is stored.

The heat exchanging body 10 is horizontal with respect to an axis 21. If the contours of the heat exchanging cylinder 10 are followed using a rightward rotating hand motion, this hand motion allows the conduit 20 to be easily pressed into or checked in the grooves 18. The insertion procedure of the conduit starts, as already mentioned, as viewed in the direction towards the first end surface 12, at the lower left back portion in the vicinity of the second end surface 13.

A holding device 22 is provided for on the second end surface 13, by means of which the heat exchanging body 10 can be attached to a rod of a stand 11 in a continuously adjustable fashion.

Figure 2:
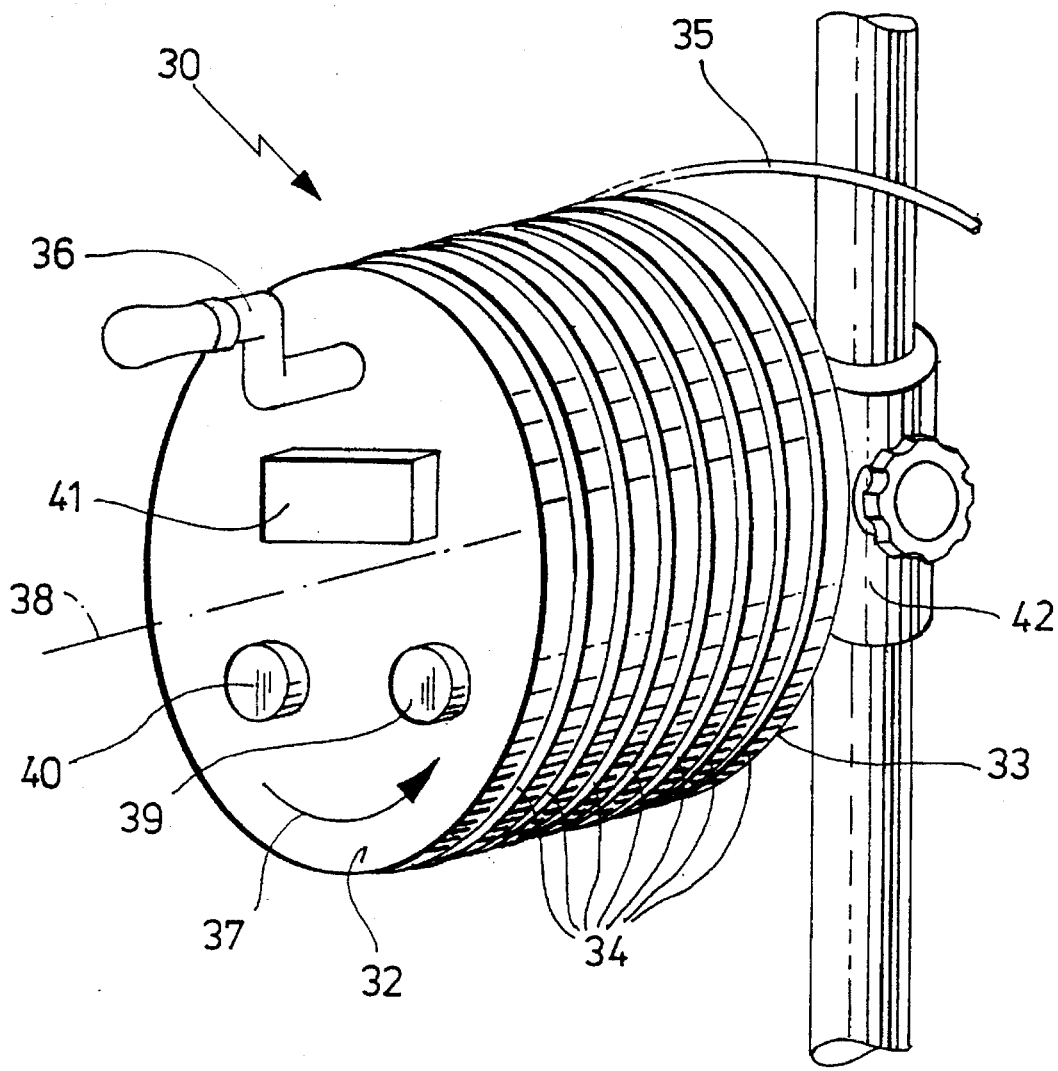
FIG. 2 shows a heat exchanging body in accordance with the invention which is configured as a straight circular cylinder with a crank for winding the conduit.

FIG. 2 shows an additional heat exchanging body 30 in accordance with the invention which is configured as a straight hollow circular cylinder. The device itself is defined by a first and a second end surface 32, 33. Grooves 34 are formed on the outer side of the heat exchanging body 30 which can hold a conduit 35 in a secure fashion within the groove region. The conduit 35 is held securely in the grooves 34. In the event that the conduit 35 is placed on the heat exchanging body 30 as shown in the figure and turned ill the direction of the arrow 37 via a crank 36 on the first end surface 32 of the heat exchanging body 30, the conduit 35 automatically winds into the screw-like grooves 34 towards tile first end surface 32. In this winding procedure the heat exchanging body 30 is directed horizontally with respect to an axis 38. It is also conceivable for the heat exchanging body 30, after winding the conduit 35 onto the heat exchanging body 30, to be pivoted into another position.

39 and 40 indicate operation elements for the apparatus on the first end surface 32 and display 41 facilitates the optical indication of operational data. A holding device 42 is provided for on the second end surface 33 by means of which the heat exchanging body 30 can be attached to objects provided therefor.

Figure 3:
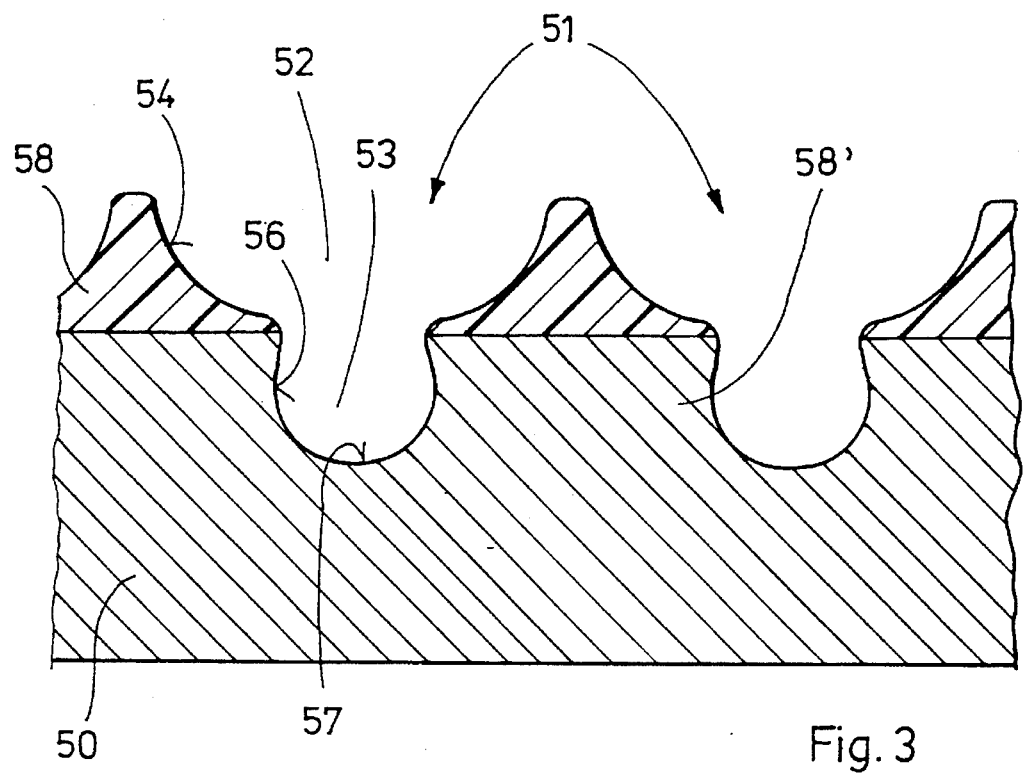
FIG. 3 shows a cross section of the shape of the groove with a first and a second groove region.
Figure 4:
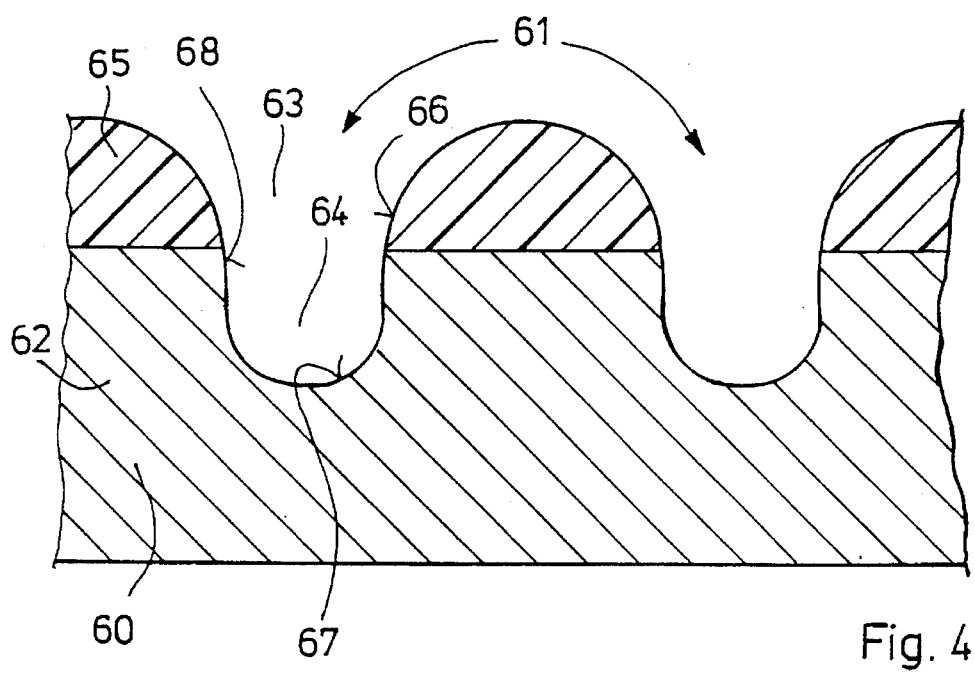
FIG. 4 shows a further embodiment of a groove in cross section with a curved opening and free strut ends which are covered with a heat insulating material.

In FIGS. 1 and 2 the grooves 18 and 34 are only suggested on the heat exchanging body 20, 30. FIGS. 3 and 4 show cross sections of possible preferred groove forms in enlarged scale as they could be configured on the heat exchanging body 20, 30.

FIG. 3 shows a cross section of a section of a heat exchanging body 50 which is made from a good heat conducting material. The figure shows two screw like grooves 51 having a first groove region 52 and a second groove region 53. The first groove region 52 is configured in a widened fashion so that a tube which is to be inserted into the groove region 53 can be guided therein without encountering any obstacles. For example, the first groove region 52 exhibits an opening which is 2.5 times larger than the outer diameter of the conduit to be inserted into the groove region 53. The first groove region 52 exhibits concave groove sides 54. This groove side shape is adapted to the tips of the finger or the thumb. The grooves 51 are separated from each other by a multiple of their width so that, when inserting the conduit, the possibility of skipping over a groove loop is prevented in the best possible manner. The size of the second groove region 53 is largely adapted to the conduit to be inserted therein. Groove sides 56 run towards the groove bottom 57 with a slight undercut so that the conduit seats in the groove region 53 with improved heat contact. The groove regions 52 and 53 are flush in plan view. The corresponding grooves 51 are separated from each other by means of struts 58, 58'. The struts 58 are made from a heat insulating material connected to a good heat conducting material of the struts 58' of the heat exchanging body 50. The struts 58 are rounded towards their free ends.

FIG. 4 shows a cross section of an additional portion of a heat exchanging body 60 having grooves 61. The grooves 61 are separated from each other via struts 62. A first groove region 63 whose groove sides run in a convex fashion, leads into a second groove region 64 which is configured as a holding groove. The conduit in which the fluid to be warmed flows, is held in a secure fashion in the second groove region 64. The heat exchanging body 60 is manufactured from a good heat conducting material and the crowns of the struts are provided with a coating 65 which is heat insulating.

The apparatus for the heating of fluids exhibits a cylindrical heat exchanging body 10 which exhibits an outer groove 18 for the insertion of a conduit 20 through which the fluid is flowing. The groove 18 forms windings w with a heat transfer length 1 per winding w. With a fixed section length L to be warmed of the conduit 20 the heat transfer length 1 per winding w is at least increased by a factor of 1.4 or the heat exchanging cylinder 10 is directed largely horizontally and the diameter of the heat exchanging body 10 is larger than 160 mm.

We claim:

1. A Medical device for warming at least one of an infusion, a transfusion, and a cleansing solution flowing through a tube means, the device comprising a cylindrical heat exchanging body having an outer groove for accepting insertion of the tube means, the outer groove comprising windings w of heat transfer length $1 \geq 52$ cm per winding and the tube means having a fixed heating length L, the outer groove comprising heat insulating means in the vicinity of an outer groove opening.

2. The device of claim 1, wherein the heat insulating means comprise one of a heat insulating material and a heat insulating coating.

3. The device of claim 1, wherein the outer groove opening is at least 1.6 times larger than an outer diameter of the tube means.

4. The device of claim 1, wherein the outer groove opening is curved and the outer groove comprises a first groove region having first groove sides for the insertion of the tube means and a second groove region having second groove sides for holding the tube means, the first groove sides having one of a concave, convex and a triangular cross section and the second groove sides being adapted to tightly surroundingly engage the conduit.

5. The device of claim 1, wherein the heat exchanging body has one of a circular and an elliptical cross section.

6. The device of claim 1, wherein the heat exchanging body is a hollow cylinder.

7. The device of claim 1, wherein the outer groove has windings describing a helical path around the outside of the heat exchanging body, the windings having a pitch which is larger than holding width of the outer groove.

8. The device of claim 1, wherein the outer groove has a groove bottom which, in plan view, lies within the outer groove opening.

\* \* \* \* \*

UNITED STATES PATENT AND TRADEMARK OFFICE
CERTIFICATE OF CORRECTION

PATENT NO. : 5,474,538
DATED : December 12, 1995
INVENTOR(S) : Axel Stihler and Wolfgang Theilacker-Beck It is certified that error appears in the above-indentified patent and that said Letters Patent is hereby corrected as shown below:

On the title page, item

"[73] Assignee: Stihler Electronic medizinische Gerate Produktions"

should be:

--[73] Assignee: Stihler Electronic medizinische Gerate Produktions- und Vertriebs-Gmbh--

Signed and Sealed this

Sixth Day of August, 1996

Attest:

BRUCE LEHMAN

Attesting Officer

Commissioner of Patents and Trademarks